US010863943B2

(12) United States Patent
Marcus et al.

(10) Patent No.: US 10,863,943 B2
(45) Date of Patent: Dec. 15, 2020

(54) METHODS AND DEVICES FOR PLACEMENT OF ELECTROCARDIOGRAM LEADS

(71) Applicant: ARIZONA BOARD OF REGENTS ON BEHALF OF THE UNIVERSITY OF ARIZONA, Tucson, AZ (US)

(72) Inventors: Frank I. Marcus, Tucson, AZ (US); Trina D. Hughes, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 229 days.

(21) Appl. No.: 16/184,030

(22) Filed: Nov. 8, 2018

(65) Prior Publication Data
US 2019/0133523 A1    May 9, 2019

Related U.S. Application Data

(60) Provisional application No. 62/583,135, filed on Nov. 8, 2017.

(51) Int. Cl.
*A61B 5/00* (2006.01)
*A61B 5/107* (2006.01)
(Continued)

(52) U.S. Cl.
CPC ............ *A61B 5/684* (2013.01); *A61B 5/1072* (2013.01); *A61B 5/6823* (2013.01); *A61B 5/0402* (2013.01);
(Continued)

(58) Field of Classification Search
CPC ..... A61B 5/684; A61B 5/1072; A61B 5/6823; A61B 5/0402; A61B 5/0408;
(Continued)

(56) References Cited

U.S. PATENT DOCUMENTS 4,583,549 A    4/1986 Manoli
4,846,194 A *  7/1989 Sabia ..................... A61B 5/107
                                                  600/594

(Continued)

FOREIGN PATENT DOCUMENTS

EP          1054621 B1      8/2010
WO     WO2015048309 A1      4/2015

OTHER PUBLICATIONS

Marcus F et al. Clinical location of the 4th and 5th intercostal spaces as a percent of the length of the sternum. Journal of Electrocardiology 51 (2018) 55-59.
(Continued)

*Primary Examiner* — Yaritza Guadalupe-McCall
(74) *Attorney, Agent, or Firm* — Nguyen Tarbet LLC

(57) ABSTRACT

Methods and devices for identifying the $4^{th}$ and the $5^{th}$ intercostal spaces for the purpose of proper placement of ECG precordial leads, regardless of the patient's height and/or weight. By calculating the sternal length, the distance between the sternal notch and the xiphoid process, the locations of the $4^{th}$ and $5^{th}$ intercostal spaces can be determined. The present invention also features devices for measuring the length and to indicate to a user the location of the $4^{th}$ and $5^{th}$ intercostal spaces based on the measured sternal length. The methods and devices provide a more accurate identification of the $4^{th}$ and the $5^{th}$ intercostal spaces resulting in proper ECG lead placement, which then facilitates accurate ECG interpretation.

20 Claims, 6 Drawing Sheets

(51) Int. Cl.
*A61B 5/0408* (2006.01)
*A61B 10/00* (2006.01)
*A61B 5/0402* (2006.01)

(52) U.S. Cl.
CPC ..... *A61B 5/0408* (2013.01); *A61B 2010/0093* (2013.01)

(58) Field of Classification Search
CPC .......... A61B 2010/0093; A61B 5/1107; A61B 5/6869; A61B 5/7217; A61B 18/1492; A61B 2017/00084; A61B 2018/00357
USPC .......................................................... 33/512
See application file for complete search history.

(56) References Cited

U.S. PATENT DOCUMENTS

| | | | |
|---|---|---|---|
| 5,868,671 | A | 2/1999 | Mahoney |
| 6,173,198 | B1* | 1/2001 | Schulze ............. A61B 5/04085 600/382 |
| 6,259,939 | B1 | 7/2001 | Rogel |
| 6,360,119 | B1 | 3/2002 | Roberts |
| 8,006,400 | B2* | 8/2011 | Gerster ................ G01G 19/445 33/512 |
| 8,721,573 | B2 | 5/2014 | Hoffmann |
| 8,881,417 | B2* | 11/2014 | Sano ........................ G01B 5/24 33/512 |
| 2005/0049515 | A1 | 3/2005 | Misczynski et al. |
| 2009/0088652 | A1 | 4/2009 | Tremblay |
| 2009/0320307 | A1* | 12/2009 | Richter .................. G01B 3/205 33/512 |
| 2010/0005675 | A1* | 1/2010 | Gerster .................. G01G 19/50 33/512 |
| 2019/0133523 | A1* | 5/2019 | Marcus ................ A61B 5/6823 |

OTHER PUBLICATIONS

Jay et al. Identification of 4th intercostal space using sternal notch to xiphoid length for accurate electrocardiogram lead placement. Journal of Electrocardiology 48 (2015) 1058-1061.

Rajaganeshan, R. et al. Accuracy in ECG lead placement among technicians, nurses, general physicians and cardiologists. The International Journal of Clinical Practice, 62(1):65-70 (2008).

Lehmann MH et al. Proposed bedside maneuver to facilitate accurate anatomic orientation for correct positioning of ECG precordial leads V1 and V2: a pilot study. Journal of Emergency Medicine, 43(4):584-92 (2012).

Kahn GM. A new electrode placement method for obtaining 12-lead ECGs. Open Heart, 2(1):e000226 (2015).

Fang, H. An improved method of electrode placement for ECG monitoring in children. Chinese Journal of Contemporary Pediatrics, 17(9):975-79 (2015).

Herman, MV. et al. Variability of electrocardiographic precordial lead placement: a method to improve accuracy and reliability. Clinical Cardiology, 14(6):469-76 (1991).

Rautaharju, PM et al. A standardized procedure for locating and documenting ecg chest electrode positions: Consideration of the effect of breast tissue on ecg amplitudes in women. Journal of Electrocardiology, 31(1):17-29 (1998).

* cited by examiner

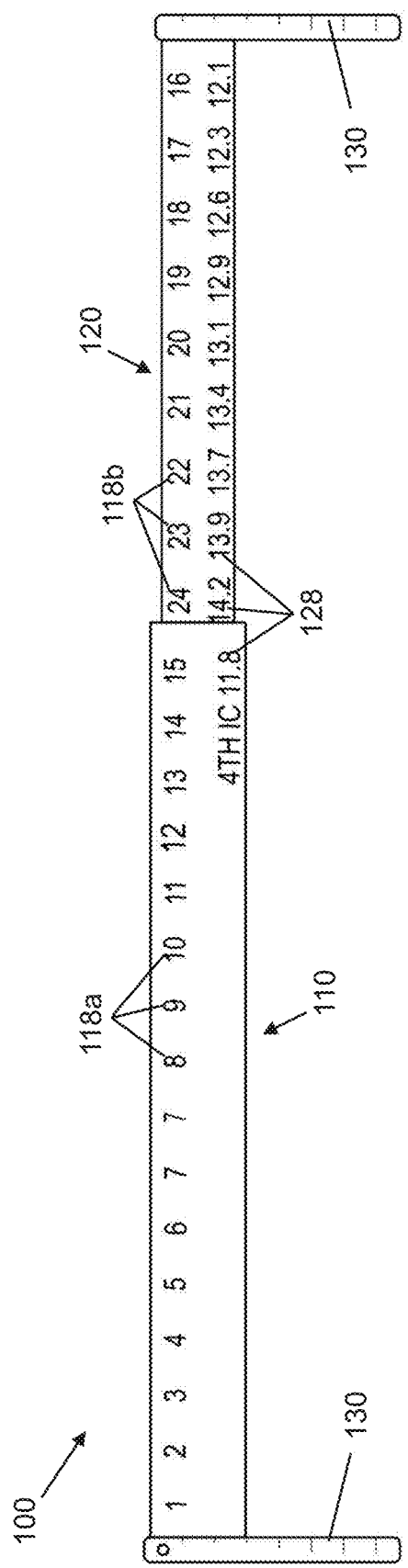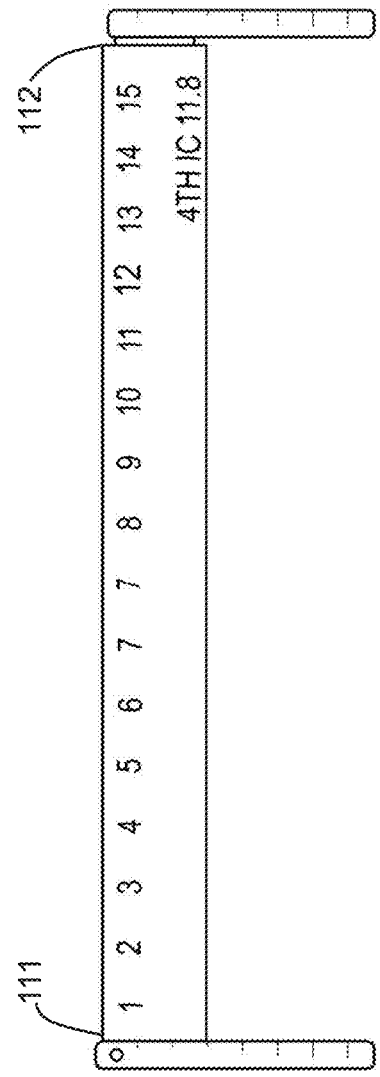
FIG. 1
FIG. 2

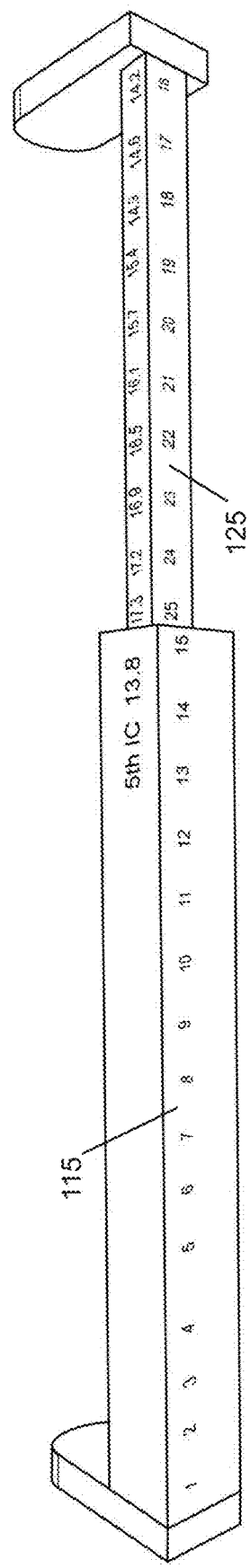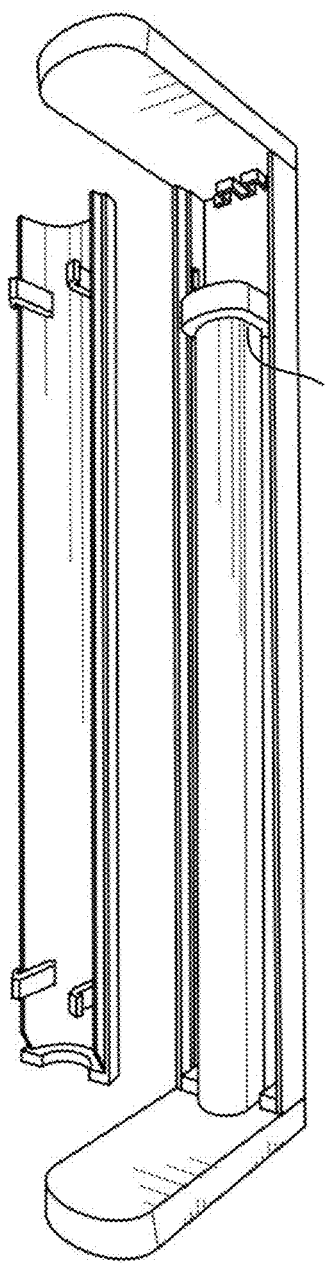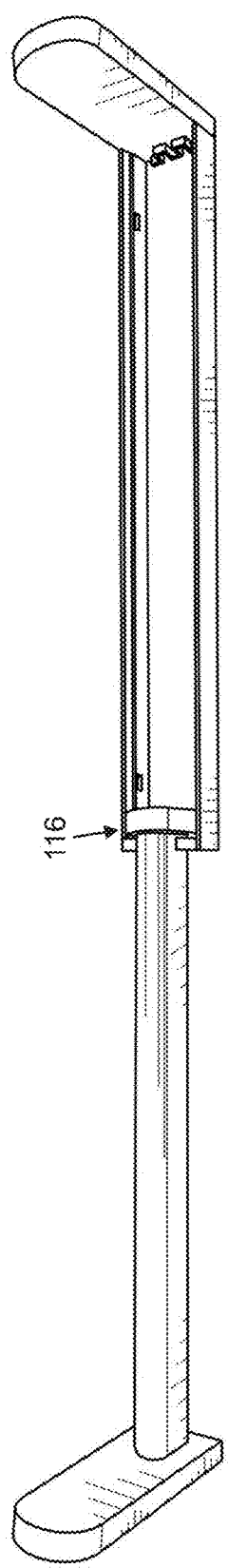
FIG. 6
FIG. 7
FIG. 8

TABLE 1: Mean Distance from Sternal Notch to the Center of the 4th Intercostal Space by CT scan and Clinically and the Percentage of this Measurement Related to the Length of the Sternum

| Sternal Length: Distance from SN to XP (cm) | Distance from SN to Center of 4th IC by CT scan (cm), N=55 | Distance from SN to Center of 4th IC clinically (cm), N=31 | Percentage of the 4th IC calculated from the length of Sternum by CT scan, N=55 | Percentage of the 4th IC calculated from the length of Sternum clinically, N=31 |
| --- | --- | --- | --- | --- |
| 15 | 11.4 | 11.8 | 76% | 77% |
| 16 | 11.8 | 12.1 | 74% | 76% |
| 17 | 12.2 | 12.3 | 72% | 72% |
| 18 | 12.5 | 12.6 | 69% | 70% |
| 19 | 12.9 | 12.9 | 68% | 68% |
| 20 | 13.3 | 13.1 | 66% | 65% |
| 21 | 14 | 13.4 | 67% | 64% |
| 22 | 14.1 | 13.7 | 64% | 62% |
| 23 | 14.5 | 13.9 | 63% | 60% |
| 24 | 14.9 | 14.2 | 62% | 59% |
| 25 | 15.2 | 14.5 | 60% | 58% |
| 26 | 15.5 | 14.8 | 59% | 57% |

Abbreviations: Intercostal Space – IC; Sternal Notch – SN; Xyphoid Process – XP
The CT scans were performed in 55 adult patients. The clinical measurements were made in 13 volunteers and in 18 patients while they were supine.

FIG. 11

| TABLE 2: Mean Distance from Sternal Notch to 5th Intercostal Space Measured Clinically and the Percentage of this Measurement to the Length of the Sternum ||| 
|---|---|---|
| Distance from SN to XP (cm) | Distance from SN to Center of 5th IC (cm) | Percentage of 5th IC to length of Sternum |
| 15 | 13.8 | 92% |
| 16 | 14.2 | 89% |
| 17 | 14.6 | 86% |
| 18 | 14.9 | 83% |
| 19 | 15.4 | 81% |
| 20 | 15.7 | 78% |
| 21 | 16.1 | 77% |
| 22 | 16.5 | 75% |
| 23 | 16.9 | 73% |
| 24 | 17.3 | 72% |
| 25 | 17.2 | 69% |
| 26 | 18 | 69% |
| Abbreviations: Intercostal Space – IC; Sternal Notch – SN; Xyphoid Process – XP |||

FIG. 12

METHODS AND DEVICES FOR PLACEMENT OF ELECTROCARDIOGRAM LEADS

CROSS REFERENCE

This application is a non-provisional and claims benefit of U.S. Patent Application No. 62/583,135, filed Nov. 8, 2017, the specification(s) of which is/are incorporated herein in their entirety by reference.

FIELD OF THE INVENTION

The present invention relates to placing precordial chest leads of the electrocardiogram (ECG) on patients, more particularly, to a sternal measurement device for accurately identifying the $4^{th}$ and $5^{th}$ intercostal spaces for lead placement purposes.

BACKGROUND OF THE INVENTION

Electrocardiology is a standard method to determine the presence of ischemic heart disease as well as to suspect abnormalities of the right and left ventricles. Additionally, recording of precordial electrocardiograms can suggest the presence of atrial enlargement as well as right and left ventricular hypotrophy. Anterior myocardial infarction can be suspected by the presence of Q waves in the anterior precordial leads or by poor progression of the height of the QRS complexes across the precordium. Electrocardiography records electrical activity of a patient's heart by placing electrodes, or leads, on the limbs and on the chest. The proper location of the chest leads are as follows: Leads V1 and V2 are placed in the $4^{th}$ intercostal space to the right and left of the sternum respectively; V4 is placed in the $5^{th}$ intercostal space at the left midclavicular line; V3 is placed midway between V2 and V4; V5 is placed at the left mid axillary line horizontal with the V4 electrode; and V6 is placed at the left anterior axillary line, horizontal with the V4 electrode.

Diagnosis may be incorrect if the precordial leads are improperly placed. Accurate placement of the leads is critical to produce accurate ECG results. Currently, palpation is commonly used to identify the intercostal spaces. However, the epidemic of obesity has markedly increased the difficulty in locating the precise positions of the precordial leads due to the increased amount of soft tissue on obese individuals. Because of the difficulty in palpating the intercostal spaces, proper lead placement is hard to achieve, even in non-obese patients.

Several approaches have been suggested to increase the accuracy of precordial lead placement. For example, one approach is to identify $2^{nd}$ interspace including the sternal notch by placing one's hand up against the base of the neck, and another approach uses a precordial lead grid. Recently, an electrode locator has been proposed to determine the correct precordial lead placement. None of these approaches have been widely adopted and the traditional approach of attempting to feel the $4^{th}$ and $5^{th}$ interspaces by palpitation of the chest wall is the dominant method for localization of the precordial leads. Hence, there is a need to resolve the issue of proper lead placement.

The present invention features methods and devices for identifying the $4^{th}$ and the $5^{th}$ intercostal spaces for the purpose of accurately placing the leads of an electrocardiogram (ECG) regardless of the patient's height and/or weight. An approach to the location of the $4^{th}$ and $5^{th}$ intercostal spaces is proposed based on a linear function of the length of the sternum. This approach using the above method may be particularly useful in obese individuals.

SUMMARY OF THE INVENTION

It is an objective of the present invention to provide methods and devices that allow for an accurate identification of the $4^{th}$ and $5^{th}$ intercostal spaces, resulting in accurate ECG lead placement and reliable ECG results, as specified in the independent claims. Embodiments of the invention are given in the dependent claims. Embodiments of the present invention can be freely combined with each other if they are not mutually exclusive.

In some aspects, the present invention features a sternal measurement device to measure the length from the sternal notch (upper end of the sternum) and the xiphoid process (lower end of the sternum) and to indicate to a user the location of the $4^{th}$ and the $5^{th}$ intercostal space based on the measurement of the sternal length. In one embodiment, the sternal measurement device may comprise a ruler base having a first end, a second end and length measurements disposed along at least a portion of its length. The length measurements correspond to a length of the ruler base from the first end to the second end. The sternal measurement device further comprises a slide base slidably connected to the ruler base. Length measurements are disposed along at least a portion of a length of the slide base. The length measurements are in ascending order from the second end (the second end being the end opposite the ruler base) to the first end of the slide base. Note the first length measurement disposed at the second end of the slide base is a unit of length greater than the last length measurement disposed on the second end of the ruler base (e.g., if the last usable length measurement disposed on the second end of the ruler base was, for example, 15 cm, the first length measurement on the second end of the slide base would be 16 cm).

In other embodiments, the device may further comprise intercostal length measurements disposed on the ruler base and/or the slide base adjacent to at least one length measurement. The "$4^{th}$ intercostal placement length" refers to the distance from the sternal notch to the $4^{th}$ intercostal space, and the "$5^{th}$ intercostal placement length" refers to the distance from the sternal notch to the $5^{th}$ intercostal space. In this way, the device shows a user the $4^{th}$ intercostal placement length (for placing the V1 and V2 leads) and/or the $5^{th}$ intercostal placement length (for placing the V4 lead). Without wishing to be bound to a particular theory or mechanism, the present invention may offer an inexpensive and effective solution for the accurate ECG identification of the $4^{th}$ and $5^{th}$ intercostal spaces. The device may also be used by technicians and as a teaching tool for those learning to accurately record ECGs.

Without wishing to limit the present invention to a particular theory or mechanism, the locations of the $4^{th}$ and $5^{th}$ intercostal spaces are related to the sternal length. As a non-limiting example, the distance from the sternal notch to the right $4^{th}$ intercostal space (herein referred to as the "$4^{th}$ intercostal placement length") is a percentage of the sternal length. For instance, the $4^{th}$ intercostal placement length may be 77% of the sternal length for a sternum measuring 15 cm.

In some embodiments, the device may further comprise flanges disposed on the first end of the ruler base and the second end of the slide base. The device may be rigid, flexible, or a combination thereof. In some embodiments, the ruler base is a tube and the slide base is slidably disposed in the ruler base. For example, the device is telescoping such that the slide base can slide in and out of the ruler base to place the device in a shortened or extended configuration. In one embodiment, the length measurements are in centimeters. In another embodiment, the intercostal length measurements are in centimeters.

According to other aspects, the present invention features methods of identifying the $4^{th}$ and the $5^{th}$ intercostal spaces from a measurement of the sternal length, which is the distance between the sternal notch and the xiphoid process. In some embodiments, the method may comprise placing the first end of a sternal measurement device (e.g., a device according to the present invention) at the sternal notch of the subject and the second end of the device at the xiphoid process of the subject. This may require sliding the slide base of the device outwardly from the ruler base of the device. The method further includes viewing a length measurement corresponding to the sternal length of the subject, and viewing an intercostal length measurement adjacent to the length measurement. In one embodiment, the length measurement may be on the slide base adjacent to the second end of the ruler base, or on the ruler base itself. In some embodiments, the intercostal length measurement includes a measurement that corresponds to the distance from the sternal notch to the $4^{th}$ intercostal space, or the $5^{th}$ intercostal space, or both measurements. In preferred embodiments, the method further comprises measuring the intercostal length measurement identified on the device downwardly from the sternal notch, thereby identifying the location of the $4^{th}$ intercostal space. In a similar way, the method further comprises measuring the intercostal length measurement identified on the device downwardly from the sternal notch to identify the location of the $5^{th}$ intercostal space.

According to further aspects, the present invention also features methods for correctly placing ECG leads on a patient or subject. In some embodiments, the method may comprise measuring a sternal length of the patient using a sternal measurement device (e.g., a device according to the present invention) and calculating a $4^{th}$ intercostal placement length and/or calculating a $5^{th}$ intercostal placement length. Again, the $4^{th}$ intercostal placement length is the distance from the sternal notch to the $4^{th}$ intercostal space of the patient, and the $5^{th}$ intercostal placement length is the distance from the sternal notch to the $5^{th}$ intercostal space of the patient. The method may further comprise placing a V1 lead at the $4^{th}$ intercostal placement length to the right of the sternum, and placing a V2 lead at the $4^{th}$ intercostal placement length to the left of the sternum. A V4 lead may also be placed at the $5^{th}$ intercostal placement length at a left midclavicular line and a V3 electrode placed midway between the V2 and V4 leads. The method may further comprise placing a V5 lead at a left mid axillary line horizontal with the V4 lead. A V6 lead may also be placed at a left anterior axillary line horizontal with the V4 lead.

Any feature or combination of features described herein are included within the scope of the present invention provided that the features included in any such combination are not mutually inconsistent as will be apparent from the context, this specification, and the knowledge of one with ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings:

FIG. 1 is a non-limiting embodiment of a sternal measurement device of the present invention shown in an extended configuration. The device may comprise two telescoping tubes where a smaller-diameter tube is inserted into a larger-diameter tube. When the device is positioned such that one end is at the sternal notch and the other end is at the xiphoid process, the length of the sternum is measured and indicated by a numerical value. Adjacent to that numerical value is another number corresponding to the location of the $4^{th}$ intercostal space. In some embodiments, a number corresponding to the $5^{th}$ intercostal placement length is also adjacent to the numerical value.

FIG. 2 shows the sternal measurement device in a shortened configuration.

FIG. 6 shows an alternative embodiment of the sternal measurement device in an extended configuration. The lower row of numbers indicates the length in cm of the sternum and the adjacent numbers in the upper row is the distance (cm) to the $5^{th}$ intercostal space.

FIG. 7 is a back view of the sternal measurement device shown in FIG. 6. A portion of the outer tube is removed to view the internal tube and sliding mechanism.

FIG. 8 is another back view of the sternal measurement device in an extended configuration with the portion of the outer tube removed.

FIG. 11 shows Table 1, which lists the values for the locations of the $4^{th}$ interspaces calculated as a linear function of the sternal length (plotted in FIG. 9).

FIG. 12 shows Table 2, which lists the values for the locations of the $5^{th}$ interspaces calculated as a linear function of the sternal length (plotted in FIG. 10).

DETAILED DESCRIPTION OF THE INVENTION

Figure 3:
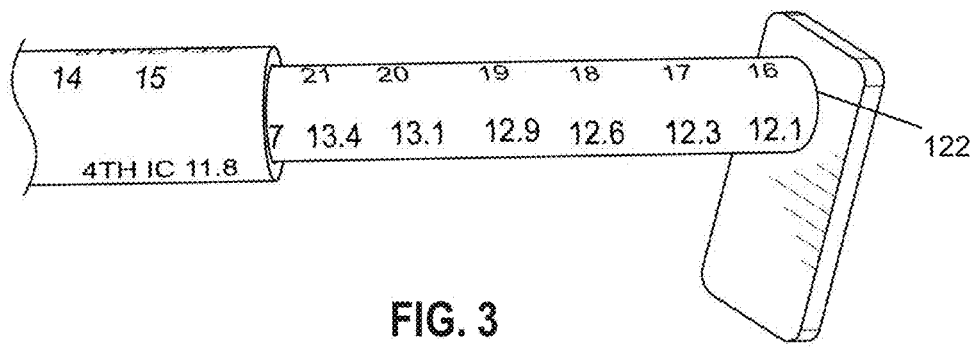
FIG. 3 is a close-up side view of the device showing an upper row of numbers indicating the length (cm) of the sternum the adjacent numbers on the lower row represents the distance (cm) to the $4^{th}$ intercostal space, as computed from a percentage of the sternal length.
Figure 4:
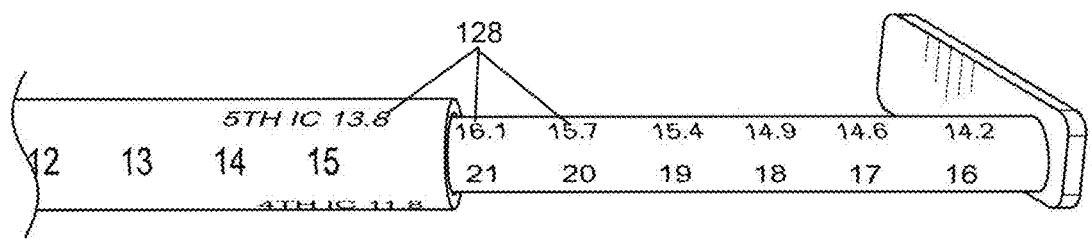
FIG. 4 is a close-up of the other side of the measuring device showing a lower row of numbers indicating the length (cm) of the sternum. The adjacent numbers in the upper row is the distance (cm) to the $5^{th}$ intercostal space, as computed from a percentage of the sternal length.

Following is a list of elements corresponding to a particular element referred to herein:
- 100 device
- 110 ruler base
- 111 first end of ruler base
- 112 second end of ruler base
- 115 surface of ruler base
- 116 stopper mechanism
- 118a first set of sternal length measurements
- 118b second set of sternal length measurements
- 120 slide base
- 121 first end of slide base
- 122 second end of slide base
- 125 surface of slide base
- 128 intercostal length measurements
- 130 flange Because the $4^{th}$ intercostal space can be difficult to locate by traditional palpation in obese, and even non-obese, patients for electrocardiogram (ECG) lead placement, the present invention provides a method and device capable of locating the $4^{th}$ intercostal space using other easily identifiable landmarks on the chest. The invention facilitates this process by measuring the sternal notch to xiphoid process distance and providing the sternal notch to $4^{th}$ intercostal space distance. This should decrease the percentage of lead misplacement leading to misdiagnoses. Furthermore, the present invention does not require specific ECG systems to use or read unique data like other "flexible" ECG systems.

The present disclosure provides data that the precordial locations of the ECG leads can be determined based on the sternal length measured from the sternal notch to the tip of the xiphoid process. As used herein, the term "sternal length" refers to the distance between the sternal notch and the xiphoid process. As used herein, the term "$4^{th}$ intercostal placement length" refers to the distance from the sternal notch to the $4^{th}$ intercostal space. As used herein, the term "$5^{th}$ intercostal placement length" refers to the distance from the sternal notch to the $5^{th}$ intercostal space.

According to some embodiments, the present invention features devices for identifying the $4^{th}$ intercostal space and/or $5^{th}$ intercostal space for the purpose of placing ECG leads, related to the patient's height and/or weight. For example, the present invention provides sternal measurement devices for measuring the sternal notch to xiphoid process length and for indicating to a user the location of the $4^{th}$ and/or the $5^{th}$ intercostal space based on the measured sternal lengths.

Referring to now to FIGS. 1-8, the sternal measurement device (100) may comprise a ruler base (110) having a first end (111) and a second end (112). The ruler base (110) is marked with a first set of sternal length measurements (118a) disposed along a surface (115) of the ruler base in ascending order from the first end (111) to the second end (112). The length measurements correspond to the length of the ruler base from its first end (111) to its second end (112). The length measurements (118a) are for measuring the sternal length (e.g., the length between the sternal notch to the xiphoid process). FIG. 1 shows the length measurements (118a) in centimeters; however the present invention is not limited to the use of centimeters. The device (100) in FIG. 1 also shows length measurements (118) from 0 or 1 cm to 15 cm. The present invention is not limited to a 15 cm long ruler base (110), e.g., the ruler base (110) may be less than 15 cm in length or more than 15 cm in length.

The ruler base (110) may be constructed in a variety of configurations. For example, the device (100) shown in FIG. 1 may be constructed such that the ruler base (110) is a tube. If the ruler base (110) is a tube, the slide base (120) may be disposed within the ruler base (110) such that the device is telescoping. In some embodiments, the ruler base (110) comprises a hollow cavity (e.g., as in the tube configuration) or a partial hollow cavity. However, the present invention is not limited to a tube-like configuration for the ruler base. In other embodiments, the ruler base (110) does not have a hollow cavity, e.g. the ruler base is solid. For example, in some embodiments, the ruler base (110) may be flat. The slide base (120) can slide underneath the ruler base (110) such that the ruler base (110) overlaps the slide base (120). In still other embodiments, as shown in FIGS. 6-8, the ruler base (110) may tubular with a portion thereof being a flattened surface.

In some embodiments, the sternal measurement device (100) may include a slide base (120) having a first end (121), a second end (122), and a second set of sternal length measurements (118b) disposed along a surface (125) of the slide base. In some embodiments, the slide base (120), e.g., the first end, is slidably housed within the inner cavity of the ruler base (110) and the second end (122) extends from the ruler base (110), e.g., in the case of the tube-shaped ruler base shown in FIGS. 1-8. In alternative embodiments, the slide base (120) slides underneath the ruler base or side to side with the ruler base.

In other embodiments, the slide base (120) may also be marked with a second set of sternal length measurements (118b) disposed along a surface (125) of the slide base for the purpose of measuring sternal length. The first sternal length measurement on the slide base (120) may be located at the second end (122), and the first sternal length measurement corresponds to the next unit of length greater than the last unit of length on the ruler base (110), e.g. the last sternal length measurement (118a) disposed on the second end (112) of the ruler base. For example, if the last unit of length on the ruler base (110) is 15 cm, then the first unit of length at the second end (122) of the slide base is 16 cm. In preferred embodiments, the second set of sternal length measurements (118b) are in ascending order from the second end (122) to the first end (121) of the slide base.

When using the device (100) for measuring sternal length, a user places the first end (110) of the ruler base (110) at the sternal notch or xiphoid process and the second end (122) of the slide base (120) at the xiphoid process or sternal notch, respectively. For example, the sternal length is the maximum sternal length measurement displayed by the device (100) when the first end (111) of the ruler base is placed at the sternal notch and the second end (122) of the slide base is placed at the xiphoid process. If the sternal length is less than or equal to the last (greatest) unit of length on the ruler base, then the ruler base is used to determine the sternal length. For example, as shown in FIG. 2, if the sternal length is measured to be the exact same length as the device (110) without the slide base (120) being extended, then the sternal length is 15 cm. If the sternal length is longer than the length of the ruler base, then the slide base (120) is extended. The greatest length shown on the slide base (120) corresponds to the sternal length. For the example shown in FIG. 5, the sternal length would be 23 cm.

In preferred embodiments, the device (100) may further comprise intercostal length measurements (128) disposed on the ruler base (110) and/or slide base (120). In some embodiments, each intercostal length measurement (128) may be positioned next to one of the sternal length measurements (118b) such that each sternal length measurement (118b) has a corresponding intercostal length measurement (128). For example, as shown in FIGS. 1-8, the intercostal length measurements may be positioned above or below the sternal length measurements. Alternatively, the sternal length measurements may be oriented such that the measurements are shown in a single column (not shown), then the intercostal length measurements may be positioned to the left or right of the sternal length measurements.

Figure 5:
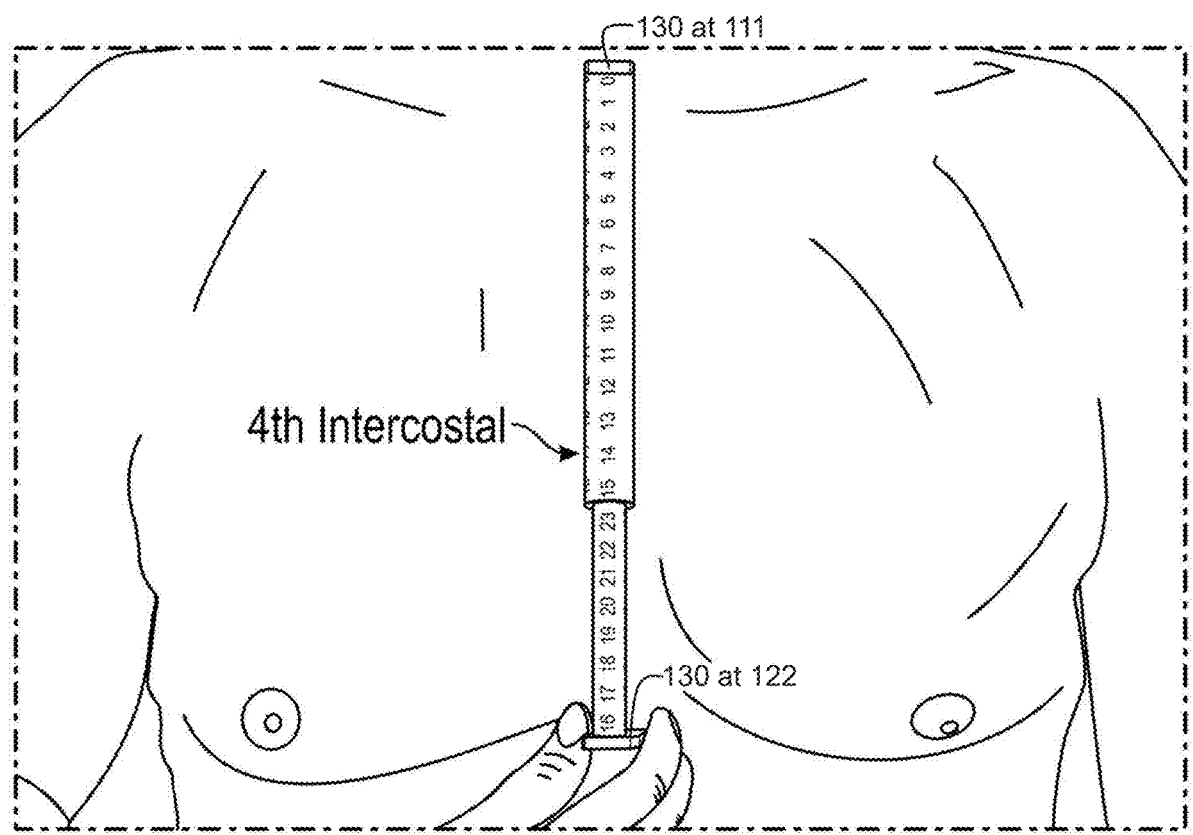
FIG. 5 is an in-use view of a sternal measurement device of the present invention. One end is placed at the sternal notch and the other end is placed at the tip of the xiphoid process to measure the length of the sternum. The sterna length measurement is indicated by a numerical value. Adjacent to that numerical value are corresponding values for the location of the $4^{th}$ and $5^{th}$ intercostal spaces.

Without wishing to limit the present invention, the intercostal length measurement may be determined by the maximum sternal length measurement. In one embodiment, the intercostal length measurements (128) may correspond to the appropriate $4^{th}$ intercostal placement length (distance between sternal notch and $4^{th}$ intercostal space). The 4th intercostal placement length indicates the location of the 4th intercostal space for placement of an electrode. For example, the length measurement (sternal length) of 23 cm shown in FIG. 5 is aligned with the intercostal length measurement of 13.9 cm. A length measurement (sternal length) of 21 cm is aligned with the intercostal length measurement of 13.4 cm.

In another embodiment, the intercostal length measurements (128) may correspond to a $5^{th}$ intercostal placement length (distance from the sternal notch to a $5^{th}$ intercostal space). The $5^{th}$ intercostal placement length indicates the location of the $5^{th}$ intercostal space for placement of an electrode. For example, the length measurement (sternal length) of 25 cm shown in FIG. 6 is aligned with the intercostal length measurement of 17.6 cm. A length measurement (sternal length) of 21 cm is aligned with the intercostal length measurement of 16.1 cm.

In preferred embodiments, a user can look at the sternal length measurement (118) to determine the $4^{th}$ and $5^{th}$ intercostal length measurements. Although the sternal length measurements and intercostal length measurements may be in centimeters, it is not limited to this unit or measurement. Alternatively, the measurements may be in inches. In some embodiments, the intercostal length measurements may be calculated based on the data in FIGS. 9-12. For instance, the intercostal length measurement (128) corresponding to the $4^{th}$ intercostal placement length may be selected from the following table depending on the sternal length measurement.

| Sternal length measurement (cm) | $4^{th}$ Intercostal length measurement (cm) |
|---|---|
| 15 | 11.8 |
| 16 | 12.1 |
| 17 | 12.3 |
| 18 | 12.6 |
| 19 | 12.9 |
| 20 | 13.1 |
| 21 | 13.4 |
| 22 | 13.7 |
| 23 | 13.9 |
| 24 | 14.2 |
| 25 | 14.5 |
| 26 | 14.8 |

As another example, the intercostal length measurement (128) corresponding to the $5^{th}$ intercostal placement length may be selected from the following table depending on the sternal length measurement.

| Sternal length measurement (cm) | $5^{th}$ Intercostal length measurement (cm) |
|---|---|
| 15 | 13.8 |
| 16 | 14.2 |
| 17 | 14.6 |
| 18 | 14.9 |
| 19 | 15.4 |
| 20 | 15.7 |
| 21 | 16.1 |
| 22 | 16.5 |
| 23 | 16.9 |
| 24 | 17.3 |
| 25 | 17.2 |
| 26 | 18 |

In some embodiments, the device (100) of the present invention may further comprise flanges (130), tabs, or other components disposed at the ends (e.g., first end of the ruler base and second end of the slide base) to anchor the device (110) at the sternal notch or xiphoid process. In other embodiments, the device (100) may further comprise a stopper mechanism (116) that stops the first end (121) of the slide base from sliding out of the ruler base, thereby preventing the slide base from completely separating from the ruler base. In FIG. 8, for example, the stopper mechanism (116) may comprise an internal lip at the second end of the ruler base, and an external ridge disposed at the first end of the slide base. The internal lip is configured to block or stop the external lip from exiting through the second end of the ruler base, thereby preventing the two bases from separating from each other when pulled to extend the device.

In some embodiments, the device (100) may be constructed from any appropriate material, e.g., PVC or other polymer, etc. Alternatively, the device may be 3D printed instead of being made out of PVC pipe. In other embodiments, the device (100) may be rigid, flexible, or comprise portions that are rigid and portions that are flexible. The present invention is not limited to the materials or configurations disclosed herein.

The ruler base and/or slide base may be constructed in a variety of sizes. For example, in some embodiments, the ruler base is 10 cm in length. In other embodiments, the ruler base is from 10 to 15 cm in length, or from 12 to 18 cm in length, or from 15 to 20 cm in length. In some other embodiments, the slide base may be from 5 to 10 cm in length, or from 7 to 12 cm in length, or from 10 to 15 cm in length.

In alternative embodiments, the sternal length measurements (118), or the intercostal length measurements (128), or both may be displayed on a digital screen instead of on the surface of the bases. For example, the device may have the sternal length measurements disposed on the surface of the bases while the intercostal length measurements may be displayed on a digital screen. As another example, both the sternal length measurements and the intercostal length measurements may be displayed on a digital screen. In yet another embodiment, the slide base and/or ruler base may have a plurality of light indicators. The light indicators may be disposed at $4^{th}$ and/or $5^{th}$ intercostal space locations along the device. For example, the light indicators may be disposed at 11.8 cm, 12.1 cm, 12.3 cm, 12.6 cm, 12.9 cm, 13.1 cm, 13.4 cm, 13.7 cm, 13.9 cm, 14.2 cm, 14.5 cm, and 14.8 cm for the possible $4^{th}$ intercostal spaces. Light indicators may be disposed at 13.8 cm, 14.2 cm, 14.6 cm, 14.9 cm, 15.4 cm, 15.7 cm, 16.1 cm, 16.5 cm, 16.9 cm, 17.3 cm, 17.2 cm, and 18 cm for the possible $5^{th}$ intercostal spaces. When the device is used to obtain a sternal length measurement, the light indicator at the intercostal space location corresponding to the sternal length measurement is activated, thereby indicating the position of the intercostal space. For instance, if the sternal length measurement is 26 cm, then the light at the 14.8 cm for the $4^{th}$ intercostal space, or the light at the 18 cm for the $5^{th}$ intercostal space, or both are activated.

According to other embodiments, the present invention the present invention features methods of identifying the location of the $4^{th}$ and/or $5^{th}$ intercostal space based on a sternal length, measured as the distance between the sternal notch and the xiphoid process. In one embodiment, a method of identifying a $4^{th}$ intercostal space in a subject may comprise providing any of the sternal measurement devices (100) described herein, placing the first end (111) of the ruler base at a sternal notch of the subject and the second end (122) of the slide base at a xiphoid process of the subject, viewing the maximum sternal length measurement displayed by the device (100), and viewing an intercostal length measurement (128) corresponding to the maximum length measurement. The maximum sternal length measurement corresponds to a sternal length of the subject. In some embodiments, the maximum sternal length measurement is either the last sternal length measurement (118a) at the second end (112) of the ruler base or the sternal length measurement (118b) on the slide base (120) that is closest to the second end (112) of the ruler base. In other embodiments, the intercostal length measurement is a $4^{th}$ intercostal placement length, which is a distance from the sternal notch to the $4^{th}$ intercostal space. The method further comprises measuring the $4^{th}$ intercostal placement length from the sternal notch to identify the location of the $4^{th}$ intercostal space in the subject.

According to yet other embodiments, the present invention provides a method of identifying a $5^{th}$ intercostal space in a subject. The method is similar to the method described for identifying the $4^{th}$ intercostal space, with the difference being that the intercostal length measurement corresponds to a $5^{th}$ intercostal placement length, which is a distance from the sternal notch to the $5^{th}$ intercostal space. The $5^{th}$ intercostal placement length is measured from the sternal notch to identify the location of the $5^{th}$ intercostal space in the subject.

According to some embodiments, the present invention further provides for a method of correctly placing ECG leads on a subject. The method may comprise providing any of the sternal measurement devices (100) described herein, measuring a length of a sternum of the subject using the sternal measurement device (100) by placing the first end (111) of the ruler base at a sternal notch of the subject and the second end (122) of the slide base at a xiphoid process of the subject, determining an intercostal length measurement (128) corresponding to the sternal length measurement, the intercostal length measurement (128) is a $4^{th}$ intercostal placement length, which is a distance from a sternal notch to a $4^{th}$ intercostal space of the subject, measuring the $4^{th}$ intercostal placement length from the sternal notch to identify the location of the $4^{th}$ intercostal space in the subject, and placing a V1 lead at the $4^{th}$ intercostal space right of the sternum, and placing a V2 lead at the $4^{th}$ intercostal space left of the sternum. In other embodiments, the method may further comprise determining a second intercostal length measurement (128) corresponding to the sternal length measurement, the second intercostal length measurement (128) is a $5^{th}$ intercostal placement length, which is a distance from a sternal notch to a $5^{th}$ intercostal space of the subject, measuring the $5^{th}$ intercostal placement length from the sternal notch to identify the location of the $5^{th}$ intercostal space in the subject, and placing a V4 lead at the $5^{th}$ intercostal space at a left midclavicular line. In yet other embodiments, the method may further comprise placing a V3 lead midway between the V2 and V4 leads, placing a V5 lead at a left mid axillary line horizontal with the V4 lead, and placing a V6 lead at a left anterior axillary line horizontal with the V4 lead.

EXAMPLE

The following is a non-limiting example of the present invention. It is to be understood that said example is not intended to limit the present invention in any way. Equivalents or substitutes are within the scope of the present invention.

In a recent report (Day et al., 2015, J Electrocardiology 48:1058-1061), CT x-rays measured the location of the $4^{th}$ interspace in 55 adults. The distance from the sternal notch to the fourth interspace was found to be a mean of 67% of the sternal length, with an overall correlation of r=0.600 (p=<0.001). The present invention has discovered that the location of the $4^{th}$ and $5^{th}$ intercostal space is related to the length of the sternum and there is a trend to a higher percent of the distance from the sternal notch to the $4^{th}$ and the $5^{th}$ intercostal spaces when there is a shorter sternal length, as shown in FIGS. 11 and 12. Without wishing to limit the present invention to a particular theory or mechanism, it is 77% of the sternal length that measures 15 cm for the $4^{th}$ intercostal space. The position of the V1 and V2 electrodes decreases to 57% when the sternal length is 26 cm. Similar data was obtained to locate the $5^{th}$ intercostal space with proper position of V4-V6 electrodes. An instrument was designed to measure the $4^{th}$ and $5^{th}$ intercostal space as a function of the sternal length.

Methods

The population included patients and healthy volunteers. The study was approved by the Human Subjects Committee. All patients signed an informed consent. A trained ECG technician and a cardiologist blindly performed the measurements on 13 adult volunteers, as well as on 18 patients. The proposed method compared palpation of the $4^{th}$ and $5^{th}$ intercostal spaces to a percentile of the sternal length. Location of the $4^{th}$ and $5^{th}$ intercostal space using a simple device was evaluated to assist in proper placement of the precordial leads to obtain accurate diagnosis.

The first measurement was obtained by the technician determining the distance from the sternal notch to the xiphoid process. Without wishing to be bound to a particular theory or mechanism, the length of the sternum can be readily measured even in obese individuals. If there is a concern of the precise location of the end of the xiphoid process, a flat pillow can be placed below the patient's back at the level of the xiphoid process to raise the sternum to assist in locating this point. The location of the $4^{th}$ intercostal space was determined by palpation. When this was located a removable marker was placed on the sternum. The distance from the sternal notch to this point was measured and the percentage of the distance from the sternal notch to the $4^{th}$ intercostal space relative to the length of sternum was calculated. The physician then independently repeated this process without knowledge of the technicians' data. If the measurement of the sternal length or the distance of the sternal notch to the $4^{th}$ intercostal space was different by 2 cm between the investigators, the measurement was made jointly and the final values were determined by consensus.

All statistical calculations were done using SPSS11. Reliability was assessed using intraclass correlation. This statistic quantifies the agreement between the technician and the cardiologist. The intraclass correlation was 0.90 initially and 0.94 when significant disparities were identified and those patients re-measured. External validity was assessed by calculating the relationship clinically between distance of the $4^{th}$ intercostal space distance to the sternal notch and the length of the sternum measured as distance from the xiphoid process to the sternal notch. These data were compared to the same relationship obtained in the previous study in which measurements were made by CT scan.

Results

Data from the CT study in Day et al. were modified by adding half the width of the $4^{th}$ intercostal space to the distance from the sternal notch to the $4^{th}$ intercostal space ($4^{th}$ intercostal placement length) to correspond to the procedure used in the clinical setting. The locations of the $4^{th}$ and $5^{th}$ interspaces were calculated as a linear function of the sternal length (plotted in FIG. 9), and the predicted values are listed FIG. 11.

Figure 9:
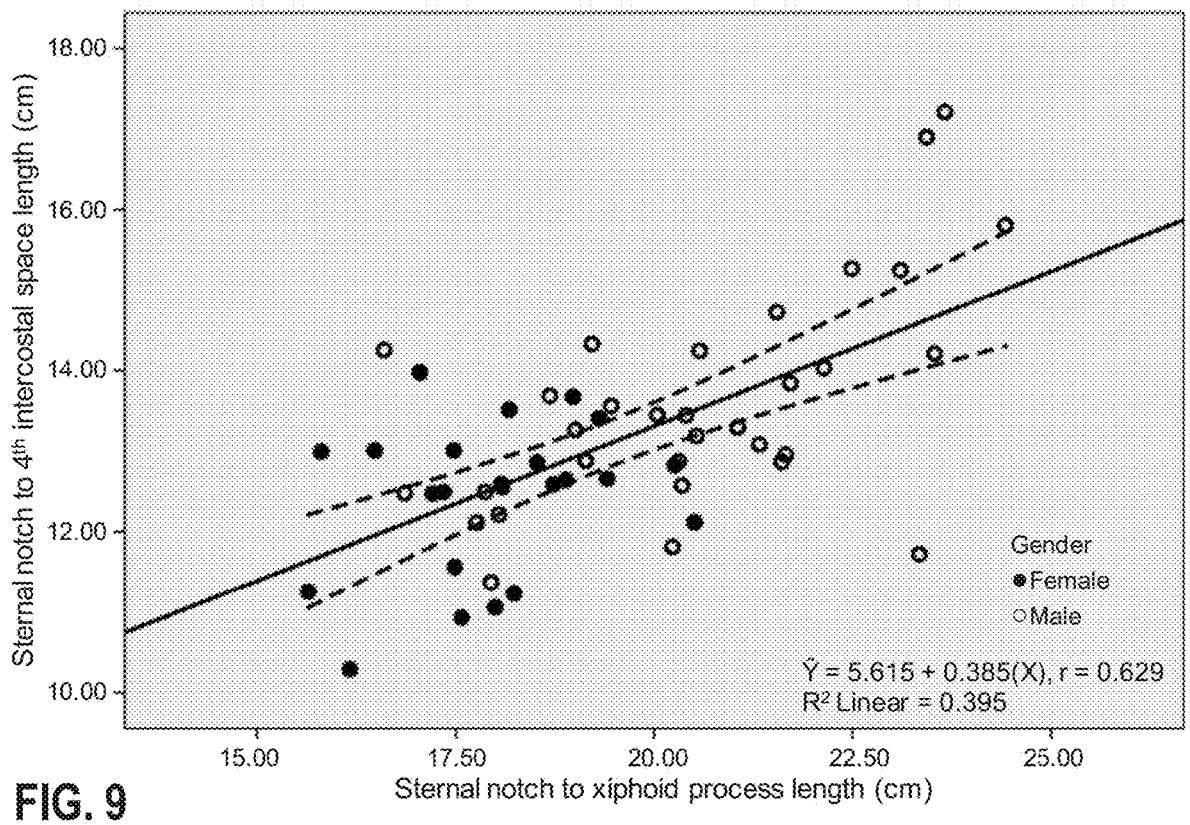
FIG. 9 shows CT measurements of the $4^{th}$ intercostal space as sternal length vs. $4^{th}$ intercostal placement length from Marcus et al. (Marcus F, Hughes T, Barrios P, and Borgstrom M. "Clinical location of the $4^{th}$ and $5^{th}$ intercostal spaces as a percent of the length of the sternum." *Journal of Electrocardiology.* 2018 January-February; 51(1):55-59. doi: 10.1016/j.jelectrocard.2017.05.006. Epub 2017 May 18). The solid line represents the best fit line, or regression line, for clinically predicting the location of the $4^{th}$ intercostal space using the sternal length. It is expressed mathematically by $Y=5.615+0.385(X)$, $r=0.629$, wherein X is the sternal length, Y is the $4^{th}$ intercostal placement length, and r is the correlation between these two distances.
Figure 10:
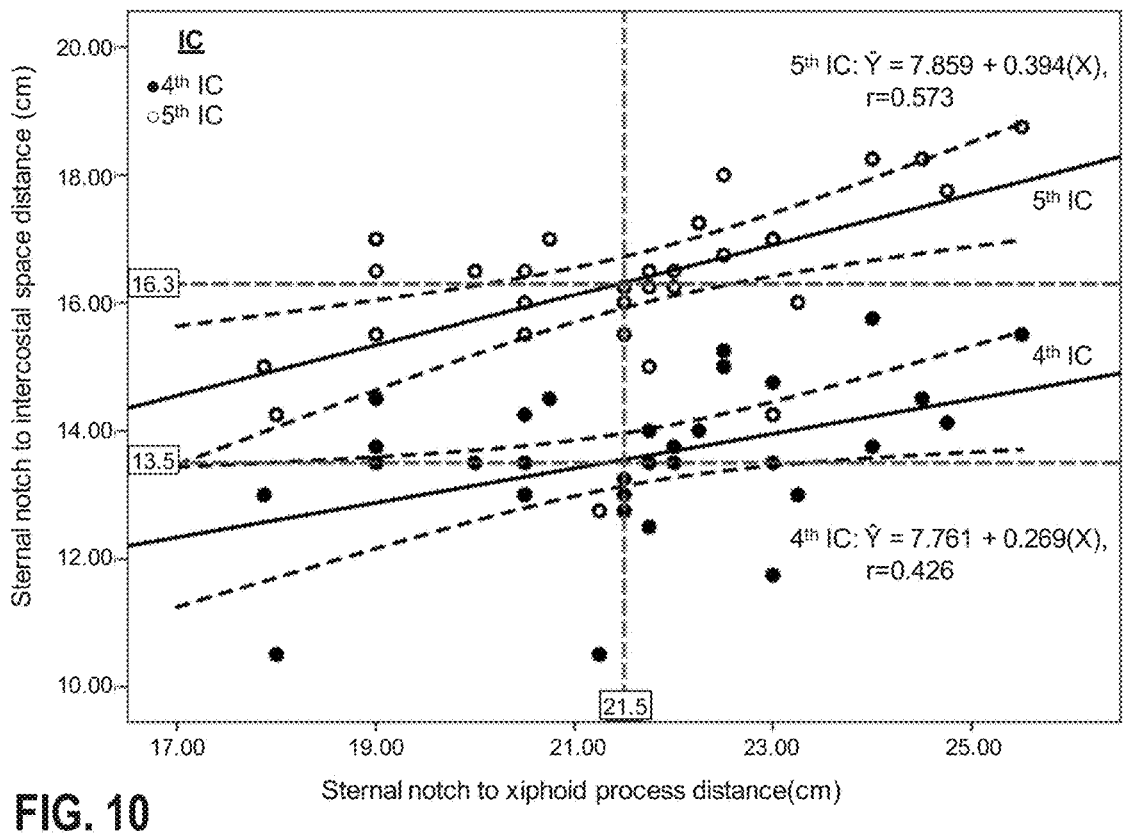
FIG. 10 shows clinical measurements of the $4^{th}$ and $5^{th}$ intercostal space from Marcus et al. The best fit solid lines are calculated by the linear functions: $4^{th}$ intercostal space: $Y=7.761+0.269(X)$, $r=0.426$; $5^{th}$ intercostal space: $Y=7.859+0.394(X)$, $r=0.573$. The dashed lines represent the 95% confidence bands around the lines of best fit.

The linear function depicted in FIG. 9 can be used to predict the $4^{th}$ intercostal placement length (distance from the sternal notch to the 4th intercostal space). As can be seen from column 4 and column 5 of Table 1 in FIG. 11, the percentage of the sternal length (distance from the sternal notch to the xiphoid process) that corresponds to the $4^{th}$ intercostal placement length (distance from the sternal notch to the 4th intercostal space) decreases as the sternal length increases, such that a single percentage does not represent the relationship between the two distances. Thus, a two parameter linear model with a proportional component and an additional constant may be useful (see caption in FIG. 1). The relationship between the $4^{th}$ intercostal placement length and the $5^{th}$ intercostal placement length from the clinical data and linear models for those relationships are shown in FIGS. 10-12. The mean $4^{th}$ intercostal placement length was 65% of the sternal length in patients with a sternal length of 20 cm and the $5^{th}$ intercostal placement length was 78%. The $4^{th}$ interspace is the correct location of V1 and V2 electrodes and the $5^{th}$ interspace identifies the correct location of V4-V6.

Discussion

The proposed method of the present invention can accurately locate the precordial ECG positions as a function of the sternal length. Facilitation of the location of the V1 and V2 electrode placement using a device, such as those shown in FIGS. 1-8, can facilitate the proper position of the V1 and V2 electrodes to enhance the diagnostic value of the ECG. As noted in the tables of FIGS. 11-12, the location of the V1 and V2 electrodes is a function of the length of the sternum. The correct location of the V1 and V2 electrodes are a smaller percent of the total sternal length with increasing length of the sternum. The tables were adjusted for this offset and the predicted values can be used as a table to determine the $4^{th}$ and $5^{th}$ intercostal distances from the sternal notch.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although the preferred embodiment of the present invention has been shown and described, it will be readily apparent to those skilled in the art that modifications may be made thereto which do not exceed the scope of the appended claims. Therefore, the scope of the invention is limited only by the following claims. Reference numbers recited in the claims are exemplary and for ease of review by the patent office and are not limiting in any way. In some embodiments, the figures presented in this patent application are drawn to scale, including the angles, ratios of dimensions, etc. In some embodiments, the figures are only representative and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A sternal measurement device (100) comprising:

a. a ruler base (110) having a first end (111), a second end (112) and a first set of sternal length measurements (118a) disposed along a surface (115) of the ruler base in ascending order from the first end (111) to the second end (112), said sternal length measurements (118a) corresponding to a length of the ruler base (110);

b. a slide base (120) slidably connected to the ruler base (110), the slide base (120) having a first end (121), a second end (122), and a second set of sternal length measurements (118b) disposed along a surface (125) of the slide base, wherein a first sternal length measurement (118b) disposed at the second end (122) of the slide base is a unit of length greater than a last sternal length measurement (118a) disposed on the second end (112) of the ruler base, wherein the second set of sternal length measurements (118b) are in ascending order from the second end (122) to the first end (121) of the slide base; and c. a set of intercostal length measurements (128) disposed on the surface (125) of the slide base, each intercostal length measurement (128) positioned next to one of the sternal length measurements (118b) such that each sternal length measurement (118b) has a corresponding intercostal length measurement (128);

wherein the sternal measurement device (100) measures a sternal length between a sternal notch and a xiphoid process, wherein the sternal length is the maximum sternal length measurement displayed by the device (100) when the first end (111) of the ruler base is placed at the sternal notch and the second end (122) of the slide base is placed at the xiphoid process, wherein the intercostal length measurement is determined by the maximum sternal length measurement.

2. The device (100) of claim 1, wherein the intercostal length measurements (128) correspond to a $4^{th}$ intercostal placement length, the $4^{th}$ intercostal placement length being a distance from the sternal notch to a $4^{th}$ intercostal space, wherein the $4^{th}$ intercostal placement length indicates the location of the $4^{th}$ intercostal space for placement of an electrode.

3. The device (100) of claim 2, wherein the intercostal length measurement (128) corresponding to the $4^{th}$ intercostal placement length is selected from the following table depending on the sternal length measurement.

| Sternal length measurement (cm) | 4th Intercostal length measurement (cm) |
|---|---|
| 15 | 11.8 |
| 16 | 12.1 |
| 17 | 12.3 |
| 18 | 12.6 |
| 19 | 12.9 |
| 20 | 13.1 |
| 21 | 13.4 |
| 22 | 13.7 |
| 23 | 13.9 |
| 24 | 14.2 |
| 25 | 14.5 |
| 26 | 14.8. |

4. The device (100) of claim 1, wherein the intercostal length measurements (128) correspond to a $5^{th}$ intercostal placement length, the $5^{th}$ intercostal placement length being a distance from the sternal notch to a $5^{th}$ intercostal space, wherein the $5^{th}$ intercostal placement length indicates the location of the $5^{th}$ intercostal space for placement of an electrode.

5. The device (100) of claim 4, wherein the intercostal length measurement (128) corresponding to the $5^{th}$ intercostal placement length is selected from the following table depending on the sternal length measurement.

| Sternal length measurement (cm) | 5th Intercostal length measurement (cm) |
|---|---|
| 15 | 13.8 |
| 16 | 14.2 |
| 17 | 14.6 |
| 18 | 14.9 |
| 19 | 15.4 |
| 20 | 15.7 |
| 21 | 16.1 |
| 22 | 16.5 |
| 23 | 16.9 |
| 24 | 17.3 |
| 25 | 17.2 |
| 26 | 18. |

6. The device of claim 1 further comprising flanges (130) disposed on the first end (111) of the ruler base (110) and the second end (122) of the slide base (120).

7. The device of claim 1 further comprising one or more intercostal length measurements (128) disposed on the surface (115) of the ruler base and positioned adjacent to the sternal length measurements (118a).

8. The device of claim 1 further comprising a stopper mechanism (116) that stops the first end (121) of the slide base from sliding out of the ruler base, thereby preventing the slide base from completely separating from the ruler base.

9. The device of claim 1, wherein the ruler base (110) is a tube and the slide base (120) is disposed within the ruler base (110) such that the device is telescoping.

10. The device of claim 1, wherein the slide base (120) slides underneath the ruler base (110) such that the ruler base (110) overlaps the slide base (120).

11. The device of claim 1, wherein the sternal length measurements and intercostal length measurements are in centimeters.

12. A method of identifying a $4^{th}$ intercostal space in a subject, comprising:
   a. providing a sternal measurement device (100) according to claim 1;
   b. placing the first end (111) of the ruler base at a sternal notch of the subject and the second end (122) of the slide base at a xiphoid process of the subject;
   c. viewing the maximum sternal length measurement displayed by the device (100), wherein the maximum sternal length measurement corresponds to a sternal length of the subject;
   d. viewing an intercostal length measurement (128) corresponding to the maximum length measurement, wherein the intercostal length measurement is a $4^{th}$ intercostal placement length, which is a distance from the sternal notch to the $4^{th}$ intercostal space; and
   e. measuring the $4^{th}$ intercostal placement length from the sternal notch to identify the location of the $4^{th}$ intercostal space in the subject.

13. The method of claim 12, wherein the maximum sternal length measurement is either the last sternal length measurement (118a) at the second end (112) of the ruler base or the sternal length measurement (118b) on the slide base (120) that is closest to the second end (112) of the ruler base.

14. A method of identifying a $5^{th}$ intercostal space in a subject, comprising:
   a. providing a sternal measurement device (100) according to claim 1;
   b. placing the first end (111) of the ruler base at a sternal notch of the subject and the second end (122) of the slide base at a xiphoid process of the subject;
   c. viewing the maximum sternal length measurement displayed by the device (100), wherein the maximum sternal length measurement corresponds to a sternal length of the subject;
   d. viewing an intercostal length measurement (128) adjacent to the corresponding maximum length measurement, wherein the intercostal length measurement is a $5^{th}$ intercostal placement length, which is a distance from the sternal notch to the $5^{th}$ intercostal space; and
   e. measuring the $5^{th}$ intercostal placement length from the sternal notch to identify the location of the $5^{th}$ intercostal space in the subject.

15. The method of claim 14, wherein the maximum sternal length measurement is either the last sternal length measurement (118a) at the second end (112) of the ruler base or the sternal length measurement (118b) on the slide base (120) that is closest to the second end (112) of the ruler base.

16. A method of correctly placing ECG leads on a subject, said method comprising:
   a. providing a sternal measurement device (100) according to claim 1;
   b. measuring a length of a sternum of the subject using the sternal measurement device (100) by placing the first end (111) of the ruler base at a sternal notch of the subject and the second end (122) of the slide base at a xiphoid process of the subject;
   c. determining an intercostal length measurement (128) corresponding to the sternal length measurement, wherein the intercostal length measurement (128) is a $4^{th}$ intercostal placement length, which is a distance from a sternal notch to a $4^{th}$ intercostal space of the subject;
   d. measuring the $4^{th}$ intercostal placement length from the sternal notch to identify the location of the $4^{th}$ intercostal space in the subject; and
   e. placing a V1 lead at the $4^{th}$ intercostal space right of the sternum, and placing a V2 lead at the $4^{th}$ intercostal space left of the sternum.

17. The method of claim 16 further comprising:
a. determining a second intercostal length measurement (128) corresponding to the sternal length measurement, wherein the second intercostal length measurement (128) is a $5^{th}$ intercostal placement length, which is a distance from a sternal notch to a $5^{th}$ intercostal space of the subject;
b. measuring the $5^{th}$ intercostal placement length from the sternal notch to identify the location of the $5^{th}$ intercostal space in the subject; and
c. placing a V4 lead at the $5^{th}$ intercostal space at a left midclavicular line.

18. The method of claim 17 further comprising:
a. placing a V3 lead midway between the V2 and V4 leads;
b. placing a V5 lead at a left mid axillary line horizontal with the V4 lead; and
c. placing a V6 lead at a left anterior axillary line horizontal with the V4 lead.

19. The method of claim 17, wherein the $4^{th}$ intercostal placement length is selected from the following table depending on the sternal length measurement:

| Sternal length measurement (cm) | $4^{th}$ Intercostal length measurement (cm) |
| --- | --- |
| 15 | 11.8 |
| 16 | 12.1 |
| 17 | 12.3 |
| 18 | 12.6 |
| 19 | 12.9 |
| 20 | 13.1 |
| 21 | 13.4 |
| 22 | 13.7 |
| 23 | 13.9 |
| 24 | 14.2 |
| 25 | 14.5 |
| 26 | 14.8. |

20. The method of claim 17, wherein the $5^{th}$ intercostal placement length is selected from the following table depending on the sternal length measurement:

| Sternal length measurement (cm) | $5^{th}$ Intercostal length measurement (cm) |
| --- | --- |
| 15 | 13.8 |
| 16 | 14.2 |
| 17 | 14.6 |
| 18 | 14.9 |
| 19 | 15.4 |
| 20 | 15.7 |
| 21 | 16.1 |
| 22 | 16.5 |
| 23 | 16.9 |
| 24 | 17.3 |
| 25 | 17.2 |
| 26 | 18. |

* * * * *